(12) United States Patent
Ott et al.

(10) Patent No.: US 8,211,052 B1
(45) Date of Patent: Jul. 3, 2012

(54) CHARGED HYDRATOR

(75) Inventors: Douglas E. Ott, Macon, GA (US);
Robert I. Gray, Macon, GA (US);
Duane Lloyd, Glasgow, MT (US)

(73) Assignee: Lexion Medical LLC, St. Paul, MN (US)

( * ) Notice: Subject to any disclaimer, the term of this patent is extended or adjusted under 35 U.S.C. 154(b) by 236 days.

(21) Appl. No.: 11/485,864

(22) Filed: Jul. 13, 2006

(51) Int. Cl.
*A61M 37/00* (2006.01)

(52) U.S. Cl. ........ 604/24; 604/26; 604/113; 128/204.17

(58) Field of Classification Search .................. 604/6.13, 604/23–26, 113, 291; 261/130, 141; 128/203.12–204.14, 204.17, 200.11–200.13, 128/201.21
See application file for complete search history.

(56) References Cited

U.S. PATENT DOCUMENTS

| | | | |
|---|---|---|---|
| 1,682,344 A | 8/1928 | Lesieur | |
| 2,579,113 A | 12/1951 | Gardner | |
| 2,830,580 A | 4/1958 | Saklad et al. | |
| 3,481,323 A | 12/1969 | Cook et al. | |
| 3,532,270 A | 10/1970 | Schoen, Jr. | |
| 3,563,381 A | 2/1971 | Edelson et al. | |
| 3,659,604 A | 5/1972 | Melville et al. | 128/203.27 |
| 3,674,010 A | 7/1972 | Falenks | |
| 3,712,298 A | 1/1973 | Snowdon et al. | |
| 3,735,559 A | 5/1973 | Salemme | |
| 3,747,598 A | 7/1973 | Cowans | 128/201.13 |
| 3,782,363 A | 1/1974 | Davis | |
| 3,809,374 A | 5/1974 | Schossow | |
| 3,870,072 A | 3/1975 | Lindemann | |
| 3,871,371 A | 3/1975 | Weigel | 128/145.8 |
| 3,885,590 A | 5/1975 | Ford et al. | |
| 3,897,682 A | 8/1975 | Brooks | |
| 3,904,849 A | 9/1975 | Lucero et al. | |
| 3,912,795 A | 10/1975 | Jackson | |
| 3,926,176 A * | 12/1975 | Winchell et al. | 600/8 |
| 3,954,920 A | 5/1976 | Heath | 261/104 |
| 3,961,626 A | 6/1976 | Houchen et al. | 128/145 |
| 3,982,095 A | 9/1976 | Robinson | |
| 3,982,533 A | 9/1976 | Wiest | |
| 4,010,748 A | 3/1977 | Dobritz | 128/203.27 |
| 4,011,288 A * | 3/1977 | Assenheimer et al. | 261/121.1 |

(Continued)

FOREIGN PATENT DOCUMENTS

DE 2810325 A1 3/1978

(Continued)

OTHER PUBLICATIONS

"cap". Merriam-Webster Online Dictionary. <http://www.merriam-webster.com/dictionary/cap>.*

(Continued)

*Primary Examiner* — Kevin C Sirmons
*Assistant Examiner* — Kami A Bosworth
(74) *Attorney, Agent, or Firm* — Jacobson & Johnson LLC (57) ABSTRACT

A charged hydration device and a method of filling the hydration device so the charged hydration that can be mounted to a medical apparatus that provides insufflation fluid to a body cavity either immediately prior to the medical procedure or during a medical procedure with the charged hydration device including an inlet and outlet for an inline connection with the medical apparatus so that an insufflation gas delivered through the charged hydration device is hydrated to prevent tissue damage to a person receiving the insufflation gas.

14 Claims, 5 Drawing Sheets

U.S. PATENT DOCUMENTS

| | | | |
|---|---|---|---|
| 4,048,992 A | 9/1977 | Lindemann et al. | |
| 4,054,622 A | 10/1977 | Lester | 261/64.1 |
| 4,063,548 A | 12/1977 | Klatt et al. | |
| 4,086,305 A | 4/1978 | Dobritz | |
| 4,101,294 A | 7/1978 | Kimura | |
| 4,101,611 A | 7/1978 | Williams | |
| 4,110,419 A | 8/1978 | Miller | |
| 4,121,583 A | 10/1978 | Chen | |
| 4,201,737 A | 5/1980 | Carden | |
| 4,207,887 A | 6/1980 | Hiltebrandt et al. | |
| 4,215,681 A | 8/1980 | Zalkin et al. | |
| 4,225,542 A | 9/1980 | Wall et al. | |
| 4,256,100 A | 3/1981 | Levy et al. | |
| 4,258,721 A * | 3/1981 | Parent et al. | 600/158 |
| 4,276,128 A | 6/1981 | Nishino et al. | 204/38 |
| 4,285,245 A | 8/1981 | Kennedy | |
| 4,288,396 A | 9/1981 | Ottestad | |
| 4,303,601 A | 12/1981 | Grimm et al. | |
| 4,355,636 A | 10/1982 | Oetjen et al. | 128/204.13 |
| 4,381,267 A | 4/1983 | Jackson | 261/104 |
| 4,401,114 A | 8/1983 | Lwoff et al. | |
| 4,430,994 A | 2/1984 | Clawson et al. | |
| 4,441,027 A | 4/1984 | Richardson et al. | |
| 4,464,169 A | 8/1984 | Semm | |
| 4,519,587 A | 5/1985 | Peckels et al. | |
| 4,532,088 A | 7/1985 | Miller | |
| 4,589,409 A | 5/1986 | Chatburn et al. | |
| 4,612,434 A | 9/1986 | Ianitelli et al. | |
| 4,621,632 A | 11/1986 | Bartels et al. | |
| 4,621,633 A | 11/1986 | Bowles et al. | 128/203 |
| 4,652,408 A | 3/1987 | Montgomery | 261/130 |
| 4,657,713 A | 4/1987 | Miller | |
| 4,670,006 A | 6/1987 | Sinnett et al. | |
| 4,674,494 A | 6/1987 | Wiencek | |
| 4,676,774 A | 6/1987 | Semm et al. | |
| 4,708,831 A | 11/1987 | Elsworth et al. | 261/130 |
| 4,715,372 A | 12/1987 | Philippbar et al. | |
| 4,715,998 A | 12/1987 | Clow | |
| 4,735,603 A | 4/1988 | Goodson et al. | |
| 4,747,403 A | 5/1988 | Gluck et al. | |
| 4,748,314 A | 5/1988 | Desage | |
| 4,773,410 A | 9/1988 | Blackmer et al. | |
| 4,773,411 A | 9/1988 | Downs | |
| 4,825,863 A | 5/1989 | Dittmar et al. | 128/203.27 |
| 4,830,849 A | 5/1989 | Osterholm | |
| 4,874,362 A | 10/1989 | Wiest et al. | |
| 4,921,642 A | 5/1990 | La Torraca | |
| 4,966,578 A | 10/1990 | Baier et al. | |
| 5,006,109 A | 4/1991 | Douglas et al. | 604/26 |
| 5,013,294 A | 5/1991 | Baier | 604/26 |
| 5,062,145 A | 10/1991 | Zwaan et al. | 392/396 |
| 5,098,375 A | 3/1992 | Baier | 604/23 |
| 5,139,478 A * | 8/1992 | Koninckx et al. | 604/26 |
| 5,144,474 A | 9/1992 | Keable et al. | |
| 5,148,801 A | 9/1992 | Douwens et al. | 128/203.16 |
| 5,179,966 A | 1/1993 | Losee et al. | 131/351 |
| 5,192,499 A | 3/1993 | Sakai et al. | 422/46 |
| 5,195,514 A | 3/1993 | Liu et al. | 128/203.17 |
| 5,246,419 A | 9/1993 | Absten | 604/26 |
| 5,318,731 A | 6/1994 | Yokoya et al. | 261/104 |
| 5,349,946 A | 9/1994 | McComb | 128/203.17 |
| 5,367,604 A | 11/1994 | Murray | 392/394 |
| 5,411,474 A | 5/1995 | Ott et al. | 604/26 |
| 5,435,298 A | 7/1995 | Anthony | 128/201.13 |
| 5,460,172 A | 10/1995 | Eckerbom et al. | 128/201.13 |
| 5,769,071 A | 6/1998 | Turnbull | 128/203.12 |
| 5,906,201 A | 5/1999 | Nilson | 128/203.16 |
| 5,964,223 A | 10/1999 | Baran | |
| 6,010,118 A | 1/2000 | Milewicz | 261/142 |
| 6,068,609 A | 5/2000 | Ott et al. | 604/26 |
| 6,095,505 A | 8/2000 | Miller | 261/130 |
| 6,102,037 A | 8/2000 | Koch | 128/203.26 |
| 6,394,084 B1 | 5/2002 | Nitta | 128/201.13 |
| 6,397,842 B1 | 6/2002 | Lee | 128/203.26 |
| 6,510,848 B1 | 1/2003 | Gibertoni | 128/201.13 |
| 6,523,356 B2 * | 2/2003 | Hasson et al. | 62/49.1 |
| 6,814,714 B1 | 11/2004 | Novak et al. | |
| 6,976,489 B2 | 12/2005 | Mantell et al. | 128/204.17 |
| 2004/0102731 A1 * | 5/2004 | Blackhurst et al. | 604/26 |
| 2005/0113797 A1 * | 5/2005 | Ott et al. | 604/506 |
| 2005/0171465 A1 * | 8/2005 | Smith | 604/26 |
| 2006/0178671 A1 * | 8/2006 | Canady | 606/49 |

FOREIGN PATENT DOCUMENTS

| | | |
|---|---|---|
| DE | 2834622 | 8/1978 |
| DE | 3139135 | 10/1981 |
| DE | 3430541 | 8/1984 |
| DE | 3615611 | 5/1986 |
| DE | 3927594 | 8/1989 |
| DE | 3932766 | 9/1989 |
| EP | 0169151 | 7/1988 |
| EP | 0274868 | 7/1988 |
| EP | 0311238 | 4/1989 |
| EP | 0350499 | 4/1993 |
| EP | 0 569 241 A2 | 6/1993 |
| EP | 0533644 | 12/1996 |
| EP | 0569241 | 12/1999 |
| EP | 0387220 | 4/2001 |
| GB | 729352 | 5/1955 |
| NL | 8702698 | 6/1989 |
| WO | WO 87/01443 | 3/1987 |
| WO | WO 89/04188 | 5/1989 |
| WO | WO 94/28952 | 12/1994 |
| WO | WO 01/41854 | 6/2001 |

OTHER PUBLICATIONS

"retain". Merriam-Webster Online Dictionary. <http://www.merriam-webster.com/dictionary/retain>.*

Douglas E. Ott, "Correction of Laparoscopic Insufflation Hypothermia," Journal of Laparoendoscopic Surgery, 1(4); 183-186 (1991).

Douglas E. Ott, "Laparoscopic Hypothermia," Journal of Laparoendoscopic Surgery, 1(3): 127-131 (1991).

M. Ogino et al., "Moisture-Conserving Efficiency of Condenser Humidifiers," Aneasthesia, 40:990-995 (1985).

Wolf D. Seufert et al, "The Liquid Barrier Filter—A New Concept to Eliminate Particulate Contaminants From Gases," Health Physics, 42(2); 209-216 (1982).

Thomas J. Poulton et al., "Humidification of Rapidly Flowing Gas," Critical Care Medicine, 9(1):59-63 (1981).

P. Whitehurst et al., "Temperature Alarm and Cut-Out System for Use with Heated Water Humidifiers," Br. J. Anaesth., 52:557-558 (1980).

Jack Chalon, et al., "Humidification in a Modified Circle System," Anesth. Analg. 58(3):216-220 (May-Jun. 1979).

G.C. Grant et al., "A New Humidifier," Anaesth. Intens. Care, 4(3):205-210 (Aug. 1976).

Valentin N. Dolorico, "A Safe Nonrebreathing System: Humidity, Sterility, Cost," Current Researches, 53(1):76-79 (1974).

Hypothermia Induced by Laparoscopic Insufflation, by Bessel et al., Surgical Endoscopy, vol. 9, 1995, pp. 791-796.

Pain Intensity Following Laparoscopy, by Korell et al., Surgical Laparoscopy & Endoscopy, vol. 6, 1996, pp. 375-379.

Influence of Gas Temperature During Laparoscopic Procedures, J.R. Bessell & G.J. Maddem, The Pathophysiology of Pneumo-peritoneum, Rosenthal et al., Springer, 1998, pp. 18-27.

Douglas E. Ott, "Contamination via Gynecologic Endoscopy Insufflation", Journal of Gynecologic Surgery, 5(2):205-208 (1989).

Brown, Stuart, PhD, "US 5,411,474 and 6,068,609 Validity Investigation", May 15, 2006, pp. 1-46.

"Computerized Insufflation—New Levels of Performance, Safety and Simplicity," Salesman Leaflet published by Snowden Pencer USA, 1992, two pages.

"Accessories for Thermoflator Moisturizing System for CO2 Gas," Salesman Leaflet published by Karl Storz-Endoskope, 1994, one page.

M. L. Texler et al., "Tumour Cell Movement During Heating and Humidification of Insufflating CO2: An In Vitro Model," Aust, N.Z. J. Surg., vol. 68, 1998, pp. 740-742.

W. G. Mouton et al., "Adelaide Trial Demonstrates Significant Reduction of Post-Operative Pain When Using Heated and Humidified CO2," Cook Medical Technology Technological Observer, Jan. 1998, pp. 1-4 and two additional pages.

D.E. Ott et al., "Reduction of Laparoscopic-Induced Hypothermia, Postoperative Pain and Recovery Room Length of Stay by Pre-Conditioning Gas with the Insuflow Device: A Prospective Randomized Controlled Multi-Center Study," Journal of the Society of Laparoscopic Surgeons, vol. 2, 1998, pp. 321-329.

Koninckx, Philippe R. et al., "The Persufflator: an insufflation device for laparoscopy and especially for CO2-laster endoscopic surgery," Human Reproduction, vol. 6, No. 9, pp. 128-129, 1991.

J. R. Bessell et al., "Humidified Gas Prevents Hypothermia Induced by Laparoscopic Insufflation—A Randomized Controlled Study in a Pig Model," Surgical Endoscopy, vol. 13, 1999, pp. 101-104.

W.G. Mouton et al., "A Randomized Controlled Trial Assessing the Benefit of Humidified Insufflation Gas During Laparoscopic Surgery," Surgical Endoscopy, vol. 13, 1999, pp. 106-108.

W. G. Mouton et al., "A Randomized Controlled Trial to Determine the Effects of Humidified Carbon Dioxide Insufflation During Thorascopy," Surgical Endoscopy, vol. 13, 1999, pp. 382-385 (abstract of publication provided).

M. Korell et al., "Pain Intensity Following Laparoscopy," Surgical Laparoscopy & Endoscopy, vol. 6, No. 5, 1996, pp. 375-379.

Siede, Dr. Werner et al., "Leitfaden and Atlas der Laparoskopie," J.F. Lehmanns Verlag Munchen.

W. G. Mouton et al., "Pain After Laparoscopy," Surgical Endoscopy, vol. 13, 1999, pp. 445-448.

J. Volz et al., "Characteristic Alterations of the Peritoneum after Carbon Dioxide Pneumoperitoneum," Surgical Endoscopy, vol. 13, 1999, pp. 611-614.

A.R. Biegner et al., "Quantification of Insensible Water Loss Associated with Insufflation of Nonhumidified CO2 in Patients Undergoing Laparoscopic Surgery," Journal of Laparoendoscopic & Advanced Surgical Techniques, vol. 9, No. 4, 1999, pp. 325-329.

S. Worcester, "Adhesions May Cause Pain in Some Women," Ob.Gyn. News, Jun. 1, 1999, one page.

V.R. Jacobs et al., "Measurement of CO2 Hypothermia During Laparoscopy and Pelviscopy: How Cold it Gets and How to Prevent It," The Journal of the American Association of Gynecologic Laparoscopists, vol. 6, No. 3, Aug. 1999, pp. 289-295.

"Safety in Laparoscopy," form the World Congress on Gynecologic Endoscopy and the 1$^{st}$ Annual Meeting of the Israel Society of Gynecological Endscopy , 2000 and made publicly available by OBGYN. net at http://www.obgyn.net/displaytranscript.asp?p.=/avtranscripts/israel2k_turner as of Apr. 6, 2004, 1999, two pages.

M.A. Reymond et al., "Feasibility of Therapeutic Pneumoperitoneum in a Large Animal Model Using a Microvaporisator," Surgical Endoscopy: Ultrasound and Interventional Techniques, 2000, abstract.

"Op-Pneu Electronic—Optimal, Rapid and Safe Filling of the Pneumoperitoneum", Salesman Leaflet published by WISAP, publish date unknown, one page.

"Flow-Therme—For Heating up Insufflation Gas to Body Temperature", Salesman Leaflet published by WISAP, publish date unknown, two pages.

"Therme-Pneu Electronic—Rapid & Safe Filling of the Pneumoperitoneum with Insufflation Gas Heated to Body Temperature", Salesman Leaflet published by WISAP, publish date unknown, three pages.

"Therme-Pneu Computer—Op-Pneu Computer", Salesman Leaflet published by WISAP, while the date of publication is unknown, it is believed that the leaflet was published prior to Jun. 30, 2000, four pages.

"Semm System," Salesman Leaflet published by WISAP, while the date of publication is unknown, it is believed that the leaflet was published prior to Jun. 30, 2000, four pages.

Victor Gomel, M.D., Foreword of the book entitled "Peritoneal Surgery," by Gere S. DiZerega, M.D., publisher unknown, while the date of publication is unknown it is believed that the Foreword was published prior to Jun. 30, 2000, pp. vii-xi.

* cited by examiner

CHARGED HYDRATOR

FIELD OF THE INVENTION

This invention relates generally to medical procedures and, more specifically, to an insufflation procedure where an insufflation gas is directed into a body cavity of a patient through a charged hydrator in a ready to use condition and that is quickly mountable to an insufflation apparatus prior to or during a medical procedure.

CROSS REFERENCE TO RELATED APPLICATIONS

None

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of a method and apparatus for conditioning gas for medical procedures is more fully shown and described in Ott et al. U.S. Pat. No. 6,068,609. Briefly, a humidification device or hydrator is attached to a medical apparatus that is adapted to receive an insufflation gas for delivery into the body of the patient. One portion of the apparatus includes a heater/hydrator that delivers humidified gas to a body cavity. The heater/hydrator is filled with a hydration liquid through a charging port. When an insufflation gas flows therethrough the heater/hydrator the gas is humidified and heated to the proper insufflation conditions.

In contrast, the present invention provides a charged hydrator that can be quickly attached to the insufflation apparatus at the time a medical procedure is about to begin without the need to charge the hydrator. As the hydrator is charged prior to the medical procedure one is ensured that the proper amount of hydration liquid as well as a fresh supply of hydration liquid is available for use in the medical procedure prior to initiation of the medical procedure. In addition, the use of a charged hydrator that can be quickly mounted to the insufflation apparatus allows one to quickly select hydrators with different hydration materials to accommodate different hydration requirements. For example, one can first select a hydration liquid that can include drugs or the like and then change the hydrator liquid to one that does not include drugs by changing the hydrator.

A further advantage of a charged hydrator is that at the time of surgery one can eliminate the steps of loading a syringe and then inserting the syringe into a charging port to add the hydration liquid to charge the hydrator since the hydration device of the present invention carries the needed hydration liquid in a ready-to-use condition and once attached can immediately humidify a gas flowing through the hydrator. A further advantage is that with the use of a charged hydrator one can select or increase the amount of initial charge of hydration liquid available for use during surgery. That is, if the surgery lasts longer than expected and more hydration liquid is needed one does not need to charge the hydrator during the surgery. Instead, the spent hydration device, which is connected to the insufflation apparatus, is quickly removed from the insufflation apparatus and a fresh hydration device is attached to the insufflation apparatus providing a virtual seamless supply of humidified gas to the patient undergoing surgery.

SUMMARY OF THE INVENTION

The invention comprises a charged hydration device that can be quickly mounted to a medical apparatus that provides insufflation gas to a body cavity during a medical procedure with the charged hydration device retaining the hydration liquid in the hydration device prior to attachment to an insufflation apparatus so that an insufflation gas delivered through the charged hydration device is hydrated to proper conditions to prevent tissue damage to a person receiving the insufflation gas.

DESCRIPTION OF THE PREFERRED EMBODIMENT

Figure 1:
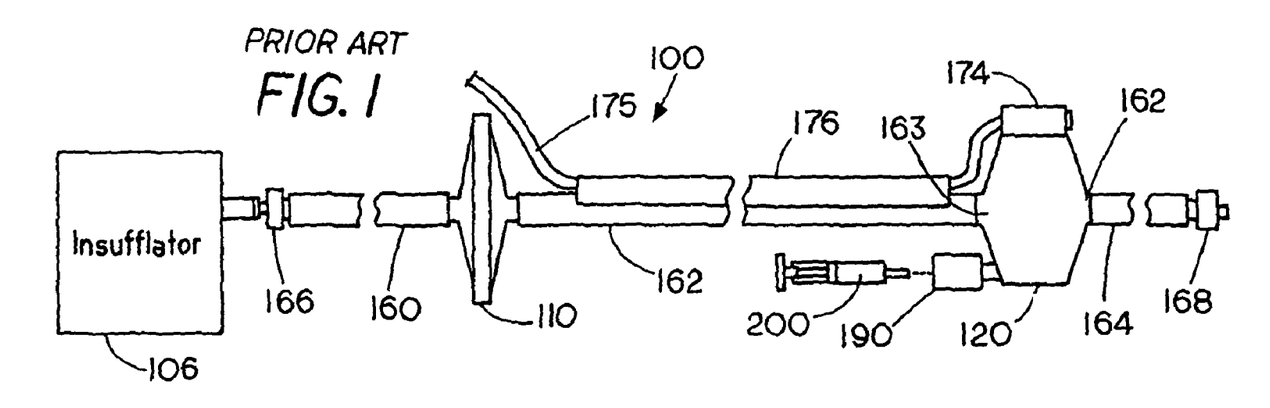
FIG. 1 shows a prior art apparatus for conditioning gas with a hydration/heater that includes a charging port and a syringe for charging the hydration/heater.

FIG. 1 is side view of a prior art medical apparatus 100 for insufflating a gas, which is shown in U.S. Pat. No. 6,068,609 and is hereby incorporated by reference. Apparatus 100, which is known as an insufflation apparatus, includes an insufflator 106 that connects to one end of tubing 160 by a connector 166. The other end of tubing 160 connects to the upstream side of a filter 110 with a second tubing 162 connected on the downstream side of filter 110. The insufflation apparatus provides an insufflation fluid such as an insufflation gas that can be inserted into the body cavity of a patient. The gas can be used to inflate the body cavity (such as the peritoneum) during endoscopic surgery. In the embodiment shown the insufflation apparatus connects to an inlet 163 of a heater/hydrator 120 that conditions the insufflation gas from the insufflator 106. Heater/hydrator 120 includes an outlet 162 that connects to tubing 164 on the outlet or downstream side of heater/hydrator 120. Tubing 164 attaches to a connector 168 that can be secured to a trocar or other instrument (such as a verres needle) that is inserted into a body cavity to deliver an insufflation fluid to a patient's body cavity. An electrical junction box 174 connects to a power source through electrical leads 175 that are held on tube 162 by a clip 176. Electrical leads (not shown) extend from junction box 174 to a heater (not shown) in heater/hydrator 120. The heating and hydration of the insufflation gas takes place in a chamber in hydrator 120. In the prior art embodiment shown in FIG. 1 the heater hydrator is filled through a charging port 190. To fill the heater/hydrator 120 one injects the needle end of syringe 200 into the charging port 190 and empty the contents of the syringe into the heater/hydrator 120, one then removes the needle end of the syringe and discards the syringe. While in preferred embodiments, the hydration device is a heater/hydrator, the invention can omit a heater in some embodiments. The invention can also be referred to as a humidifier or a heater/humidifier in some embodiments.

The present invention provides a charged ready-to-use hydrator that can be used instead of a hydrator with a charging port on the hydrator (although some embodiments can still contain a charging port) and can avoid in some instances the use during surgery of a syringe to inject hydration liquid into a charging port. The charged ready-to-use hydrator 10 of the present invention can be stored separately from the insufflation apparatus 100 but can be connected to an insufflation apparatus prior to surgery. In addition a spent charged hydrator can be replaced by connecting a fresh charged hydrator to the insufflation apparatus on an as needed basis thus avoiding on-the-go syringe charging of the hydrator. For example, if a medical procedure should take longer than anticipated and the hydration liquid in the hydrator is spent, then one can quickly remove the spent hydrator and replace the spent hydrator with a fresh charged hydrator by merely coupling a new charged hydrator to the insufflation apparatus. In addition, if the insufflation fluid contains a medication that is being injected with the insufflation fluid and a different medication is to be used during the procedure, one can disconnect the unspent hydrator and insert a different charged hydrator with a different medication (or which does not contain any medication). In some embodiments, the hydrator can come pre-charged but a charging port can be provided to add additional liquid (if necessary) during the surgery.

Figure 2:
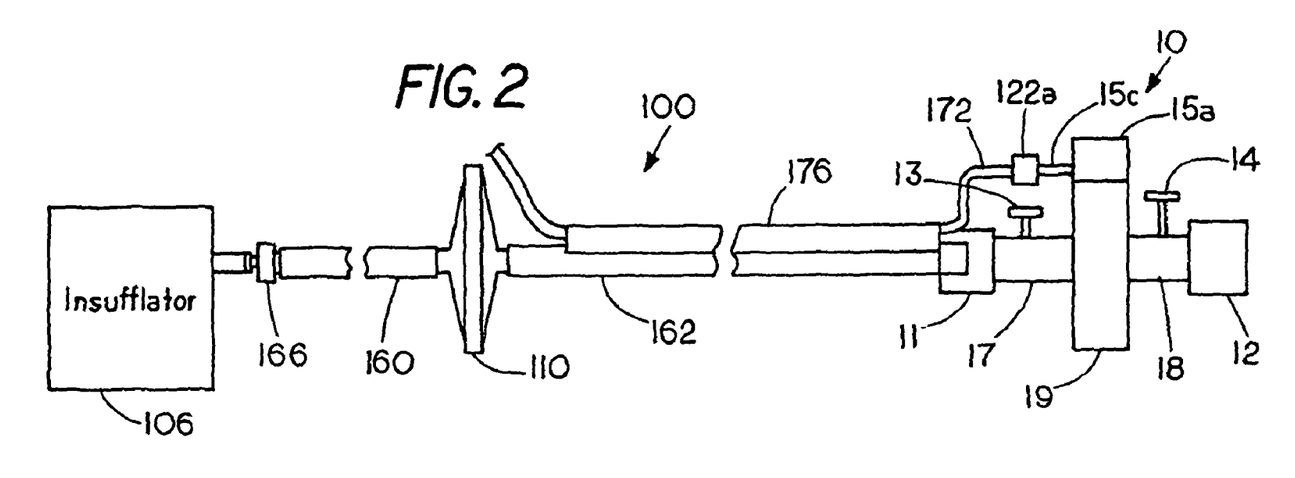
FIG. 2 shows an apparatus for gas with a charged or ready-to-use hydrator coupled to the apparatus for conditioning gas.

FIG. 2 is a side view of a medical apparatus 100 with a charged or ready-to-use hydrator 10 of the present invention in fluid communication with the medical apparatus 100. Ready-to-use hydrator 10 can include a housing 19 with an inlet 17, which comprises a cylindrical tube, connected to an upstream side of housing 19 and an outlet 18, which also comprises a cylindrical tube, connected to the downstream side of housing 19. Inlet and outlet can be formed integral with housing 19 or be separate pieces connected thereto. In the embodiment shown the ready-to-use hydrator 10 includes an internal heater (not shown) to heat the hydration fluid in the ready-to-use hydrator 10 to a desired temperature for insertion into the body cavity of a patient.

In some embodiments, the heater can be omitted. In some embodiments, the heater can be internal to housing 19, while in other embodiments, the heater can be external to housing 19, such as, for example, mounting on the exterior of housing 19, or mounted within or external to inlet 17 or outlet 18. The heater can or can not be controlled by temperature control circuitry internal or external to housing 19. In some embodiments, the temperature control circuitry can seek to keep the temperature of gas within or exiting ready-to-use hydrator 19 within a particular fixed range of temperatures, while in other embodiments the temperature range will be adjustable by the user. The temperature control circuitry can communicate with a temperature sensor internal or external to ready-to-use hydrator 10 and which can measure temperature directly or indirectly.

In some embodiments, the hydrator can have a humidity sensor (not explicitly shown) contained anywhere within ready-to-use hydrator 10 or downstream therefrom to provide an indication of the humidity of the gas output from ready-to-use hydrator. The humidity sensor can measure humidity directly or indirectly. In some embodiments, the humidity sensor can be connected to circuitry that responds to the humidity sensor by shutting down the ready-to-use hydrator 10 or sounding an alarm if the humidity drops below a specific level.

Ready-to-use hydrator 10 can include an absorbent material to hold the humidifying agent and/or a drug agent within chamber 19. Alternatively, liquids can be held in chamber 19 by membranes and an absorbent material can be omitted. In other embodiments, both membranes and an absorbent material can be used.

Inlet 17 can includes a quick connect tubing coupling 11 that one can sealingly connect or disconnect to an end of an insufflating tube 162 on the insufflator apparatus 100. Alternatively, any type of coupling or other device capable of being attached to tubing can be used to connect inlet 17 to tubing that directly or indirectly connects to insufflator 106. The coupling could be a threaded coupling or a smooth coupling, for example. In this embodiment, the inlet 17 includes a closure member 13 comprising a mechanical valve that can open and close a fluid passage in inlet 17. Any type of valve capable of opening and closing to prevent fluid flow could be used without departing from the scope of the invention. In some embodiments, the valve can be omitted. Other methods of achieving closure of inlet 17 can also be used. Similarly, the outlet 18, which is on the downstream side of housing 19, can include a closure member 14 comprising a mechanical valve that can open or close a fluid passage in outlet 18. Options such as those discussed for closure member 13 are applicable for closure member 14 as well. Some embodiments can have one closure member or no closure members. In some embodiments, closure members can be included at the entrance to or within housing 19, rather than in inlets or outlets to the space inside of housing 19. The closure members 13 and 14 in the closed condition can prevent or greatly reduce the flow of fluids (liquids or gasses) in or out of hydrator 10. On the other hand when closure members 13 and 14 are in the open condition the insufflation gas can flow though hydrator 10 to generate a properly hydrated insufflation gas that can be delivered to a patient's body cavity In some embodiments, none, one or both of closure members can comprise a cardboard or foil seal attached with an adhesive to the inlet/outlet respectively of ready-to-use hydrator 10. Such a seal could be made of different materials as well. In some embodiments, a cap (e.g. a threaded cap or a cap held on with a lip) can cover such a seal. Thus, ready-to-use hydrator 10 could be sealed at one or both ends the way that a plastic bottle of oil, drug products, glues, paints, and food products are often sealed. Alternatively, the seal might be held in place by a threaded cap but not be attached with an adhesive. Small bottles of hobby paint, for example, often use a threaded cap with a cardboard liner to seal the paint bottle. Note that the invention is not limited to the use of a single sealing mechanism and multiple sealing mechanisms can be used without departing from the scope of the invention. Thus, valves and other sealing mechanisms could be used in combination. For example, ready-to-use hydrator 10 can have one or more seals at its inlet and also have a valve along the inlet and a membrane within or at the entrance to the space inside housing 19. Any combination of the foregoing can be used and combination can be used on the outlet side of the device.

Figure 3:
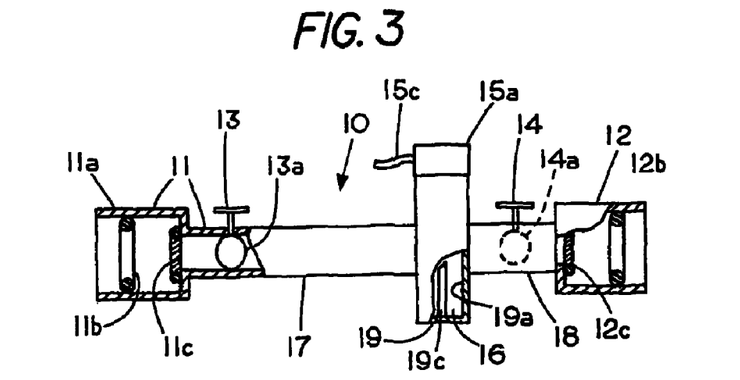
FIG. 3 shows an isolated view of the ready-to-use hydrator of the present invention carrying a hydration liquid with the hydrator connectable to an insufflation apparatus for on-site conditioning of an insufflation gas without having to charge the hydrator.

FIG. 3 is an isolated view of one embodiment of a charged or ready-to-use hydrator 10. A junction box 15*a* having an electrical lead 15*c* connects to an external power source (not shown) through electrical leads 172 (FIG. 2) to supply electrical power to a heater 16 in the hydrator 10. Alternatively, a battery or other power source within housing 19 or connected to housing 19 could be used. In embodiments with temperature feedback control, such electrical leads can also connect to a temperature sensor in accordance with the discussion above. An optional electrical connector 122*a* (FIG. 2) can allow one to quickly connect or disconnect the electrical leads 172 from the electrical leads 15*c* extending from junction box 15*a*. Connector 122*a* (FIG. 2) can provide for quick electrical connection or electrical disconnection of ready-to-use hydrator 10 from insufflation apparatus 100. In this embodiment, insufflation apparatus 100 can include temperature feedback control circuitry and a power source for heater 16. Such circuitry is optional (as discussed above) and can be contained within insufflator 106 or contained within a separate housing. While the charged hydrator 10 shown in FIG. 3 includes heater 16 the insufflation fluid can through other means be maintained at the proper insufflation temperature without the use of an internal heater in the hydrator 10.

Located at the upstream side of charged hydrator 10 is a first tubing coupling or coupler 11, which is preferably a quick connect tubing coupling that allows a user to quickly attach the inlet 17 of the heater/hydrator 10 to the tubing 162 of insufflation apparatus 100. Similarly, a second tubing coupling or coupler 12, which is located on the downstream side of charged hydrator, is also preferably a quick connect coupling that allows a user to quickly attach the outlet 18 of the heater/hydrator 10 to an apparatus (e.g. a trocar or verres needle or tubing leading thereto) that is to be inserted into a body cavity of a patient for purposes of insufflating the patient's body cavity. The tubing couplings 11, 12 can be luer locks, threaded members, or any other type of coupling without departing from the scope of the invention.

FIG. 3 shows a cutaway side view of the housing 19 of ready-to-use hydrator 10. In this embodiment, the ready-to-use hydrator 10 includes a housing 19 having a hydration chamber 19*a* therein with a heater 16 and a hydration pad 19*c*. Housing 19 can contain one or more additional chambers without departing from the scope of the invention. The chamber has an inlet passage and an outlet passage for gas to pass through the chamber to be humidified. In some embodiments, an optional recharge port into the chamber (not explicitly shown) can be included either on the chamber itself, on inlet 18, outlet, 19, or in tubing leading to inlet 17 or leading from outlet 18. Such a recharge port could be used to inject additional humidifying liquid or a drug (or both) into ready-to-use hydrator 10. The upstream side of this embodiment of ready-to-use hydrator 10 includes a first tubing coupling 11 that on one end contains a closure member such as a mechanical shutoff valve 13 having a plate 13*a* that can be rotated in a transverse direction to block or substantially block the flow passage in inlet 17 and rotated in an axial direction to allow fluid to flow through the flow passage in first tubing coupling 11. Thus, opening valve 13 by rotating the throat plate 13*a* from a flow condition that is substantially perpendicular to the flow axis of the flow passages blocks fluid flow therethrough and rotation throat plate 13*a* to a flow condition substantially parallel to a flow axis of flow passage 17 allows insufflation gas to flow into the inlet 17 and the hydration chamber 19*a* in housing 19. When the valve 13 is in the closed condition it not only prevents or substantially prevents fluid from flowing through inlet 17 but also prevents or substantially prevents the insufflation fluid from flowing out of the hydrator 10.

In this embodiment, the downstream side of housing 19 includes outlet 14 with a throat plate 14*a* that can be rotated in a transverse direction substantially perpendicular to a flow axis to block or substantially block the flow passage in outlet 18 and in an axial direction substantially parallel to a flow axis to allow fluid to flow through outlet 18. Thus, when the valves 13 and 14 are in an open condition the insufflation gas can flow through inlet 17, through ready-to-use hydrator 10 and out outlet 18. Similarly, when the valve 14 is in the closed condition it prevents or substantially prevents flow of hydration fluid through hydrator 18 but it also prevents or substantially prevents the insufflation fluid from flowing out of the ready-to-use hydrator 10. The use of closure members such as shut off valves 13 and 14 on the hydrator can allow one to maintain a hydration liquid in ready-to-use hydrator 10. Chamber 19*a* can include a pad or wick 19*c* to release the hydration liquid in the gas in the hydration chamber 16 when the ready-to-use hydrator 10 is placed in use. The hydration pad 19*c* can retain the hydration liquid in the ready-to-use hydrator 10 in a ready-to-use condition for when the ready-to-use hydrator 10 is placed in fluid communication with both the insufflation apparatus 10 and the instrument (e.g. trocar or verres needle) that is inserted into the patient. In some embodiments, the inlet and outlet can be angled or the valves can be angled such that the valve is not substantially perpendicular or parallel to flow. Any valve orientation can be used without departing from the scope of the invention.

One end of first tubing coupling 11 can include a coupler 11*a* having an annular sealing member 11*b*, such as an "O ring" to form sealing engagement with tubing 162 from insufflation apparatus 100. A closure member comprising a first punctureable seal 11*c* can extend across the fluid passage in inlet 17 and a closure member comprising a second punctureable seal 12*c* can extend across the fluid passage on outlet 18. Seal 11*c* could also be placed on the open end of first tubing coupling 11 so that the seal would maintain the upstream internal components of the first tubing coupling 11 and ready-to-use hydrator 10 in a sealed condition prior to use. Similarly, outlet 18 can include a coupler 12 like coupler 11*a* having a sealing ring 12*b* and a punctureable seal 12*c* that functions to maintain the downstream portions of hydrator 10 in a sealed condition. Thus seals 11*c* and 12*c* are additional closure members that can be used to retain the hydration liquid in the charged hydrator. In some embodiments, seals 11*c* and 12*c* (or other sealing members) can be resealable seals such that a needle and syringe can be used to inject liquid therethrough but which are sealed after the needle is withdrawn. A small luer cap with a resealable material, for example, could be used on each end of ready-to-use hydrator 10.

In operation of one embodiment, an operator first removes ready-to-use hydrator 10 from a pouch and attaches coupler 11*a* to one portion of a gas insufflation tube of the insufflation apparatus 100. If the first tubing coupling 11 includes a seal such as seal 11*c* the seal can be either punctured prior to attachment to the insufflation apparatus 100 or the insufflation apparatus can contain a member for piercing the seal 11*c* when the coupler 11*a* connects to the insufflation apparatus 100. Similarly, the coupler 12 can connect to a tube, trocar, verres needle, or other apparatus for directing insufflation fluid into the body cavity of a patient. One can puncture any seal 12*c* prior to connection or using a member for piercing the seal contained on the device to which ready-to-use hydrator 10 is connected. Once the hydrator 10 is connected, the valves 13 and 14 (if present) can be opened to provide a fluid path through the hydration device 10 to allow the insufflation gas from the medical apparatus to flow through the hydration device 10 and into a body cavity with the insufflation gas humidified (and/or heated) to the proper level to avoid tissue damage. In some embodiments, the valves can be open while the device is being connected.

Figure 4:
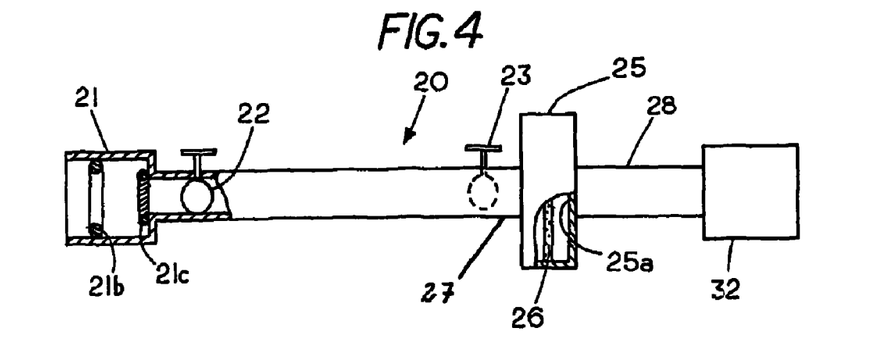
FIG. 4 shows an alternate embodiment of the hydrator wherein the hydration liquid is stored in an inlet upstream of the hydration chamber of the hydrator.

In the ready-to-use hydrator 10 of FIG. 3 the hydration liquid can then be dispersed from a pad or wick 16 in the housing 15. FIG. 4 shows an alternate embodiment of a hydration device 20 wherein the hydration liquid (and/or drug) is held in the inlet 21 between a first closure member or valve 22 and a second closure member or valve 23. Similarly, in this embodiment one can attach the coupler 21 to one portion of the tube of the insufflation apparatus and the other end to a tube (or trocar or verres needle) for directing insufflation fluid into the body cavity of a patient. In this embodiment the hydration liquid can be retained in the inlet and separate from the hydration pad or wick 26. The opening of valve 23 can allow hydration liquid to flow into the pad 26 in chamber 25a which is located in housing 25. The medical gas flowing through chamber 25a is humidified by the presence of the hydration liquid located therein. The embodiment of FIG. 4 allows one to visually observe the amount of liquid in the hydration device if the inlet 27 is formed of see-through plastic (or other material) as well as maintain the hydration pad 26 located in chamber 25a in dry condition until the hydration device is placed into use. Once the insufflation procedure is to begin one merely opens valve 23 to allow the hydration liquid to flow into the hydration chamber 25a where the liquid can humidify the insufflation gas flowing through hydration chamber 25a. Valve 22 can be opened to allow the hydration liquid to flow. Thus the embodiment of FIG. 4 allows one to store the hydration liquid separate from the hydration pad or wick that can be used to transfer the hydration liquid into the insufflation gas to bring the insufflation gas to the proper humidity. In addition if the elongated inlet 27 is made of a material with sufficient transparency the presence of the hydration liquid can be ascertained by a visual inspection.

Figure 3A:
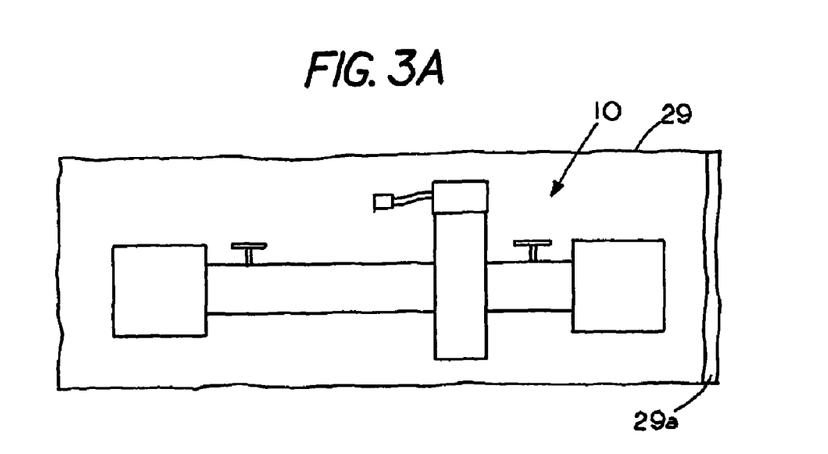
FIG. 3A shows the charged hydrator of FIG. 3 in a sealed enclosure.

FIG. 3A shows the charged hydrator 10 of FIG. 3 in a sealed package or pouch 29 to prevent contamination of the charged hydrator prior to insertion into the medical apparatus. Package 29 can preferably be a see through plastic package or the like with a sealed closure region 29a to present condition of the charged hydrator 10. When the charged hydrator is to be installed one breaches package 29, removes the charged hydrator 10 and installs the charged hydrator 10 in the appropriated medical apparatus. The sealed pouch 29 provides a sterile enclosure and can be made from a variety of materials that are capable of preventing ingress of containments into package 29.

The embodiment of FIG. 4 can also include any of the options for valves or other sealing members discussed above in connection with FIG. 3. It can also include any of the options for connection. For example, the illustrated embodiment includes a coupler 21 having an O-ring 21b and a punctureable sealing member 21c on one end and a coupler 32 on the opposite end of hydration device 50. In some embodiments with punctureable sealing member 21c, valve 22 might be omitted. More or less valves can be included on each of the inlet 27 and outlet 28 of the hydration device 20 without departing from the scope of the invention. For example, this embodiment could include nothing at the outlet or could include one or more of a membrane, a valve, a punctureable seal, a removable seal (e.g. foil or cardboard or a cap), a combination thereof, or multiples of each option. The same options apply to the inlet. The embodiment of FIG. 4 can also have any of the options discussed above with respect to heating (or can not have heating), humidification sensing, humidification (pads or no pads), recharge ports, etc.

Figure 5:
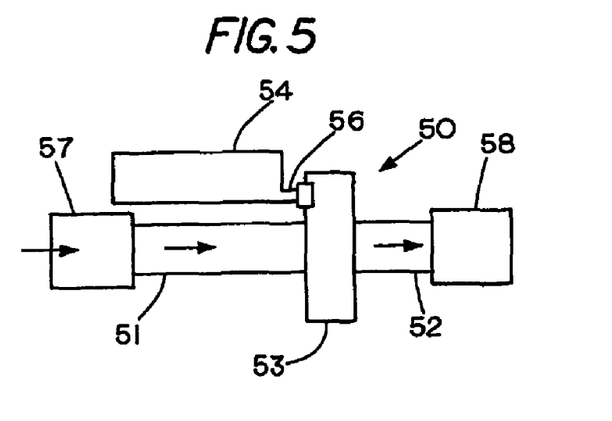
FIG. 5 shows a hydrator with a pouch carrying a hydration liquid that can be transferred from the pouch to the hydrator.

FIG. 5 shows an embodiment of the invention wherein the hydration device 50 includes an inlet 51 having a coupler 57 an outlet 52 having a coupler 58 and a housing 53 with the housing including an access port 56 for fluid connection to a container 54 that holds the hydration liquid. In this embodiment the charge of hydration liquids contained in container 54 is transferred into a hydration chamber in housing 53 through the fluid coupling 56. If the container 54 is flexible one can squeeze container 54 to deliver the hydration liquid therein to the hydration chamber in housing 53. On the other hand the container can be hard and could be transferred through other means such as gravity. In order to maintain the hydration liquid in the housing 53 after the hydration liquid has been transferred to hydration chamber a one-way valve (not shown) can be included in housing 53 to prevent back flow into the container 54. A membrane could also be included between container 54 and the chamber. All of the options discussed above with respect to FIGS. 1-4 could be used with this embodiment. For example, the embodiments of FIGS. 3 and 4 could be modified to include the container 54 of FIG. 5 wherein different fluids were contained within each. For example, container 54 could be used, when necessary, to provide a drug while hydration fluid was stored within the hydrator separately. That way, the drug could be provided for portions of a surgical procedure, but not necessarily the whole procedure.

Figure 6:
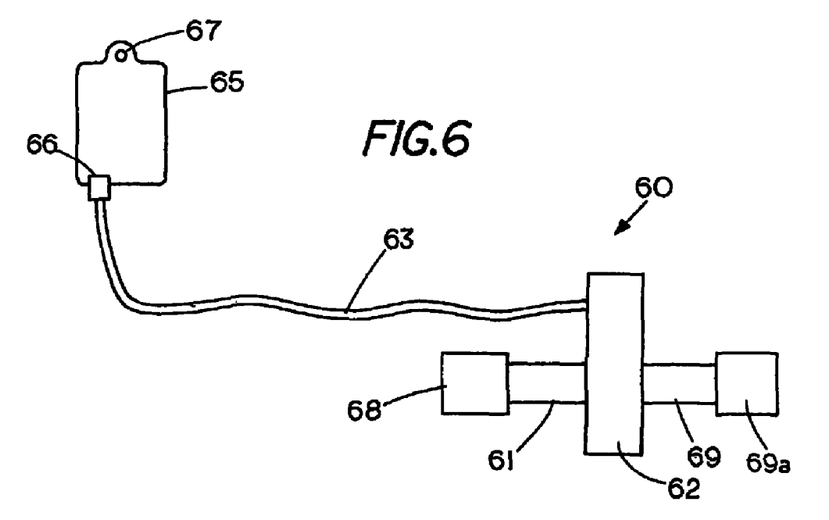
FIG. 6 shows a hydrator being supplied with hydration liquid through a gravity feed system.

FIG. 6 shows an embodiment wherein the hydration device 60 includes a housing 62 with a hydration chamber therein and an outlet 69 with coupler 69a for connection to the medical apparatus and a coupler 68 with inlet 61 for connection to an insufflation apparatus. A tube 63 extends from hydration chamber in hydration housing 62 to a liquid reservoir or container 65, which can include an eye 67 for hanging the container of hydration liquid on a support. The tube 63 connects to remote reservoir 65 through a coupling 66 so that hydration liquid can flow under the influence of gravity from container 65 into the hydration chamber in the hydration housing 62. This embodiment allows one to fill the housing with hydration fluid under the influence of gravity and by conventional liquid transfer mechanisms that are commonly found in operating rooms. Tube 63 can be bonded to housing 62 or can be removably attachable using a fitting (not explicitly shown) on housing 62. Tube 63 can run into the interior of housing 62 in some embodiments. All of the options discussed above with respect to FIGS. 1-5 could be used with this embodiment. Like the FIG. 5 embodiment, container 65 could include a drug and the embodiments of FIGS. 3 and 4 could be modified such that container 65 supplies a drug while hydration fluid is kept within a pre-charged hydration device in any of the manners discussed above.

Figures 7, 8:
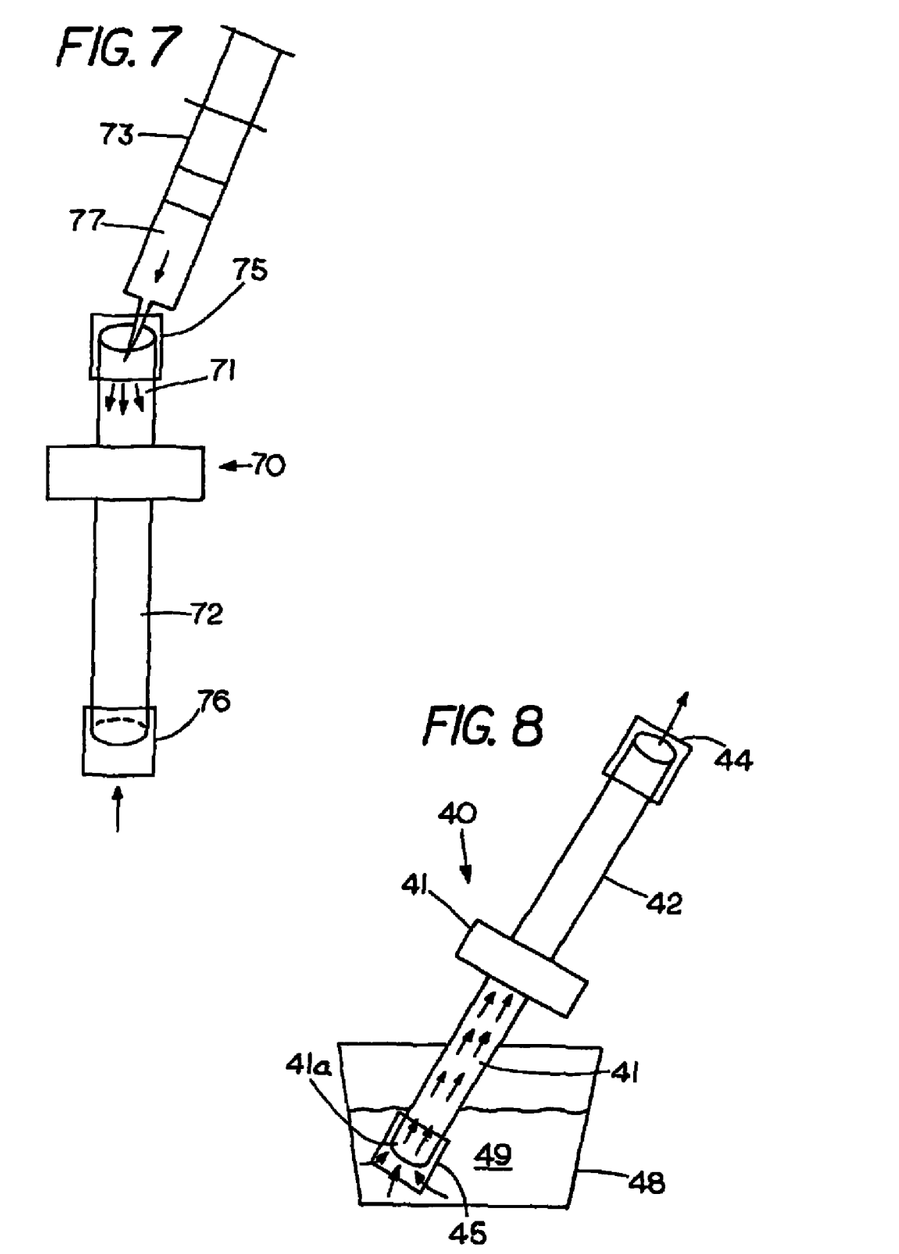
FIG. 7 shows a hydrator being charged prior to sealing and attachment to an apparatus for insufflating a gas.
FIG. 8 shows a hydrator being charged prior to sealing and attachment to an apparatus for insufflating a gas through suction of hydration liquid into the hydrator.

FIG. 7 shows a method of either filling or charging the hydration device 70 or adding another liquid such as a medicine to the hydration device 70 during the manufacturing process or immediately prior to use if it is desired that the humidification device not be precharged from the manufacturer or if it is desired to add another liquid to a precharged device. In this embodiment the hydration device 70 includes an inlet 71 with a coupling 75 and an outlet 72 with a coupling 76. The hydration liquid 77 is inserted into the inlet 71 of the hydration device 70 with a syringe 73 that allows one to meter a precise amount of hydration liquid or other liquids into the hydration device. The hydration material could also be injected into coupling 76. For example, one can add hydration liquid 77 or one can separately add a medicine to the hydration liquid. Once the hydration liquid is added a member including a punctureable seal, such as shown in FIG. 3, can be placed over the outlet to seal the hydration liquid in the chamber.

In some embodiments, the liquid can be injected through a resealable sealing member as discussed above. In other embodiments, the liquid can be injected through a puncturable seal just prior to using the device in a medical procedure. Any of the options discussed above with respect to FIGS. 1-6 can be used in connection with this embodiment.

FIG. 8 shows how a hydration device 40 can be charged through a suction process. That is the inlet 41a having coupler 45 is placed in a hydration liquid 49, such as water, which is held in container 48. By drawing a vacuum on outlet 42 which has a coupler 44 the hydration liquid 49 can be drawn into a hydration chamber in housing 41. The unit can then be installed on the medical apparatus or punctureable seals can be placed over the inlet and outlet to retain the hydration liquid therein in the event that the use of the charged device is not imminent. This embodiment allows one to provide for on site filling of the hydration while the hydration device is separate from the insufflation apparatus 10.

Figure 9:
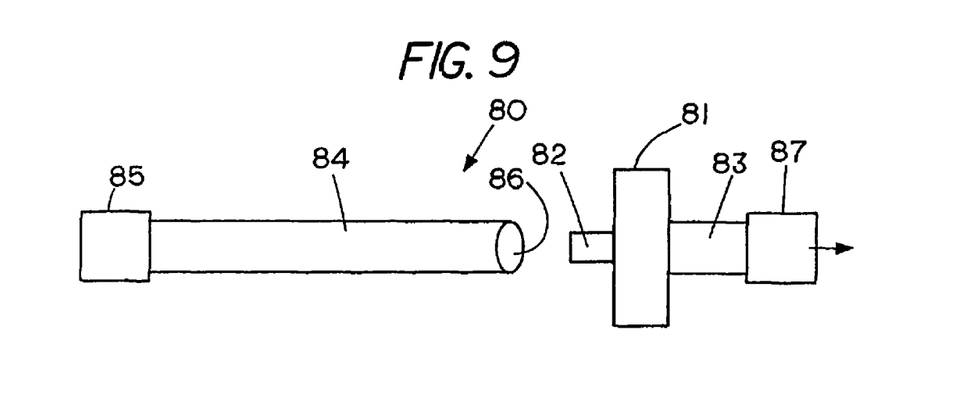
FIG. 9 shows an inlet holding a hydration liquid with the inlet connectable to a hydration chamber of a hydrator.

FIG. 9 shows a further embodiment of the invention wherein the hydration device 80 comprises two parts, a hydration tube 84 and a hydration housing 81 having an outlet 83 with a coupling 87 for connection to a medical apparatus. The other side of housing 81 includes a member 82 for attachment to hydration tube 84. In the embodiment of FIG. 9 the hydration liquid is contained in inlet hydration tube 84 and the attachment of coupler 85 to the medical apparatus establishes fluid communication on one end and the attachment of the other end 86 to member 82 provides for fluid communication to housing 81 through member 82. The entire unit including hydration tube 84 and hydration housing 81 can then be secured to the medical apparatus to provide for humidifying liquid.

The housing 81 could be modified as in FIG. 5 or 6 to provide another path for liquid into the housing 81. Inlet 84 could be configured using any of the options discussed above in connection with FIGS. 1-8 for sealing and coupling. For example, inlet 84 can include one or more valves, one or more sealing members and/or one or more membranes. Sealing members can include any of the options discussed above including threaded caps, seals secured with an adhesive, puncturable seals, and resealable seals. The liquid could be pre-charged within inlet 84. Inlet 84 could be packaged separately or within the same package as housing 81 and its other structure. These same options also apply to FIG. 10 and a filter can be included internal or external to any of the embodiments disclosed herein. In some embodiments, the outlet could be configured like the inlet illustrate in FIG. 9. In such embodiments, the liquid would be transferred from the outlet to the chamber before connection of the whole apparatus to the insufflator.

Figure 10:
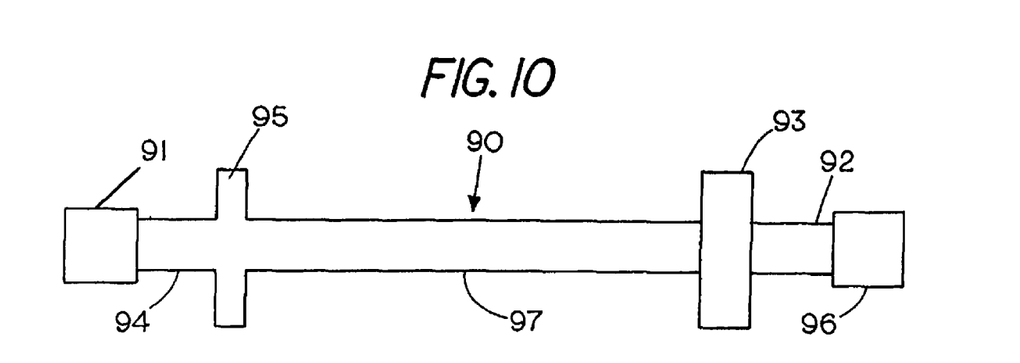
FIG. 10 shows an inlet with a filter and a hydration chamber connected thereto to permit quick attachment of a charged hydrator to an apparatus for insufflating a gas.

FIG. 10 shows a hydration device 90 that carries a filter 95 as well as a hydrator housing 93 as part of the charged hydration device 90. Hydration device 90 includes a coupler 91 secured to an inlet 94 and an outlet 92 with a coupler 96 secured thereto. Any of the coupler and sealing options discussed above can be used in connection with this embodiment as well. Inlet tubing 97 can connect filter 95 with hydrator housing 93 to provide a hydration device 90 with a flow through passage for attachment to an insufflation apparatus. A filter 95 as part of the hydration device 90 allows one to simultaneously attach a fresh filter 95 and a charged hydrator with a hydration liquid to a medical apparatus. In other words, if a doctor replace the hydrator during a procedure, the hydrator includes a fresh filter.

All of the options discussed above with respect to the heater, humidifier, humidification sensing, ports, sealing members, connectors, etc. can be used in connection with any of the embodiments of the invention. In some embodiments, a single closure could be used along with atmospheric pressure to retain the liquid within the hydrator.

In addition to the apparatus the present invention includes method of insufflating a body cavity with an insufflating gas comprising the steps of connecting an insufflator 106 to a gas source (not explicitly shown); connecting the insufflator 106 through tubing 160/162 (which can or can not include filter 110) to a ready-to-use hydration device (with any of the options discussed herein), inserting a device (such as a trocar, tube or verres needle) into a body cavity to supply gas thereto; and connecting the ready to use hydrator to such a device. When the insufflator supplies gas, the ready-to-use hydration device can hydrate and/or heat the gas and supply such treated gas to the device for entry into the body cavity.

The invention is designed to retain most of the fluid within the ready to use hydrator before the hydrator is used. Small amounts of fluid can evaporate and pass through the walls of a membrane or other sealing member without departing from the scope of the invention. A sealing member should preferably be selected that prevents the vast majority of fluid from evaporating or flowing out of the hydrator prior to use of the hydrator during a reasonable shelf life where a pre-packaged pre-charged hydrator is used.

Thus one embodiment of the invention comprises a gas hydration device including a housing having a hydration chamber, an elongated inlet to the hydration chamber operable to provide a path for fluid flow into the hydration chamber and wherein the elongated inlet is operable to receive a gas for hydration; an outlet from the hydration chamber; and a hydration liquid retained within the elongated inlet by a first closure member and a second closure member.

A method of the invention comprises insufflating a body cavity with an insufflating gas comprising the steps of; connecting an insufflator to a hydrator, the hydrator comprising a hydration liquid and having an inlet, an outlet, a first closure member preventing discharge of substantially all of the hydration liquid from the inlet prior to the hydration device being attached to another apparatus, and a second closure member preventing discharge of substantially all of the hydration liquid from the outlet prior to the hydration device being attached to another apparatus; connecting the hydrator to a trocar to deliver gas into a body cavity; and delivering gas to the body cavity from the insufflator through the hydration device which humidifies the gas prior to providing gas to the trocar.

We claim:

1. An endoscopic surgical device comprising:
   a sealed hydration device including a housing having a hydration chamber, the hydration chamber having an inlet permitting the flow of a gas into the hydration chamber and an outlet permitting the flow of gas out of the hydration chamber when said hydration device is in use;
   a fixed charge of a hydration liquid housed within the hydration device;
   a first closure member and a second closure member preventing discharge of the hydration liquid from the hydration device when the hydration device is not attached to another device; and a first coupler and a second coupler for connecting and de-connecting said hydration device from the rest of said endoscopic surgical device during a surgical procedure wherein the first closure member comprises a first valve and the second closure member comprises a second valve with the first and second valves each located between the first coupler and the second coupler.

2. The endoscopic surgical device of claim 1 including a puncturable seal located between the first coupler and the first valve.

3. The endoscopic surgical of claim 2 including a second puncturable seal located between the second coupler and the second valve.

4. The endoscopic surgical of claim 3 wherein the charge of hydration liquid housed within the hydration device includes at least one drug.

5. The endoscopic surgical device of claim 4 further comprising a heater located within the hydration chamber to heat gas flowing through the hydration device.

6. The endoscopic surgical device of claim 5 wherein the first valve and the second valve are located between the inlet and the hydration chamber.

7. The endoscopic surgical device of claim 6 wherein the charge of hydration liquid is located between the first valve and the second valve.

8. The endoscopic surgical device of claim 7 including a filter located between the first coupler and the second coupler.

9. The endoscopic surgical device of claim 8 including a junction box connected to the hydration device, the junction box having an electrical lead connected to an external power source to supply electrical power to a heater located in the hydration device.

10. The endoscopic surgical device of claim 9 wherein the gas comprises carbon dioxide.

11. A surgical device comprising:
    an insufflator providing a source of insufflation gas to a pierced opening in a body;
    a hydration device including a housing having a hydration chamber,
    an elongated inlet to the hydration chamber operable to provide a path for fluid flow into the hydration chamber and wherein the elongated inlet is operable to receive a gas for hydration,
    an outlet from the hydration chamber,
    a first coupler and a second coupler for connecting and de-connecting said housing from the rest of the surgical device during a surgical procedure,
    a first closure member and a second closure member located between the first coupler and the hydration chamber, and
    a charge of a hydration liquid retained within the elongated inlet by the first closure member and the second closure member;
    a filter; and
    a trocar.

12. The surgical device of claim 11, wherein the elongated inlet is made of a material with sufficient transparency such that presence of hydration liquid can be ascertained by a visual inspection.

13. The surgical device of claim 11, wherein the second closure member comprises a valve.

14. The surgical device of claim 11 wherein the insufflation gas comprises carbon dioxide.

\* \* \* \* \*

UNITED STATES PATENT AND TRADEMARK OFFICE
CERTIFICATE OF CORRECTION

| | | |
|---|---|---|
| PATENT NO. | : 8,211,052 B1 | |
| APPLICATION NO. | : 11/485864 | |
| DATED | : July 3, 2012 | |
| INVENTOR(S) | : Ott et al. | |

It is certified that error appears in the above-identified patent and that said Letters Patent is hereby corrected as shown below:

Claims:

Claim 3, col. 11, line 11 "The endoscopic surgical" should read --The endoscopic surgical device--

Claim 4, col. 11, line 14 "The endoscopic surgical" should read --The endoscopic surgical device--

Claim 4, col. 11, line 15 "hydration liquid" should read --the hydration liquid--

Claim 11, col. 12, line 18 "chamber, and" should read --chamber--

Claim 12, col. 12, line 26 "hydration liquid" should read --the hydration liquid--

Signed and Sealed this
Eleventh Day of September, 2012

David J. Kappos
*Director of the United States Patent and Trademark Office*